(12) United States Patent
Levine et al.

(10) Patent No.: US 7,991,472 B2
(45) Date of Patent: Aug. 2, 2011

(54) SYSTEMS AND METHODS FOR DIAGNOSING AN IMPLANTABLE DEVICE

(75) Inventors: Paul A. Levine, Santa Clarita, CA (US); Hanbiao Wang, Los Angeles, CA (US); Bonian Dai, Temple City, CA (US); Robert E. Smith, Jr., Bradbury, CA (US)

(73) Assignee: Pacesetter, Inc., Sylmar, CA (US)

( * ) Notice: Subject to any disclaimer, the term of this patent is extended or adjusted under 35 U.S.C. 154(b) by 312 days.

(21) Appl. No.: 12/247,841

(22) Filed: Oct. 8, 2008

(65) Prior Publication Data
US 2010/0087891 A1 Apr. 8, 2010

(51) Int. Cl.
*A61N 1/00* (2006.01)
(52) U.S. Cl. .......................................................... 607/27
(58) Field of Classification Search ............... 607/27–29, 607/62, 63
See application file for complete search history.

(56) References Cited

U.S. PATENT DOCUMENTS

| | | | |
|---|---|---|---|
| 4,788,980 A | 12/1988 | Mann et al. |
| 4,940,052 A | 7/1990 | Mann et al. |
| 4,969,467 A | 11/1990 | Callaghan et al. |
| 5,184,615 A | 2/1993 | Nappholz et al. |
| 6,129,746 A | 10/2000 | Levine et al. |
| 6,243,606 B1 | 6/2001 | Mann et al. |
| 6,259,950 B1 | 7/2001 | Mann et al. |
| 6,263,244 B1 | 7/2001 | Mann et al. |
| 6,285,908 B1 | 9/2001 | Mann et al. |
| 6,295,471 B1 | 9/2001 | Bornzin et al. |
| 6,311,089 B1 | 10/2001 | Mann et al. |
| 6,366,812 B1 | 4/2002 | Levine et al. |
| 6,389,316 B1 | 5/2002 | Bornzin et al. |
| 6,408,210 B1 | 6/2002 | Bornzin et al. |
| 6,430,441 B1 | 8/2002 | Levine |
| 6,477,417 B1 | 11/2002 | Levine |
| 6,546,288 B1 | 4/2003 | Levine |
| 6,584,354 B1 | 6/2003 | Mann et al. |
| 6,594,523 B1 | 7/2003 | Levine |
| 6,618,622 B1 | 9/2003 | Mann et al. |
| 6,721,600 B2 | 4/2004 | Jorgenson et al. |
| 6,721,601 B1 | 4/2004 | Bornzin et al. |
| 6,731,985 B2 | 5/2004 | Poore et al. |
| 6,766,197 B1 | 7/2004 | Levine |
| 6,792,307 B1 | 9/2004 | Levine et al. |
| 6,925,326 B1 | 8/2005 | Levine et al. |
| 6,928,362 B2 | 8/2005 | Meaney |
| 6,934,587 B1 | 8/2005 | Bornzin et al. |
| 6,950,704 B1 | 9/2005 | Bradley |
| 7,031,773 B1 | 4/2006 | Levine et al. |
| 7,149,569 B1 | 12/2006 | Fain |
| 2002/0120307 A1 | 8/2002 | Jorgenson et al. |

(Continued)

FOREIGN PATENT DOCUMENTS

WO   03077822 A2   9/2003

(Continued)

*Primary Examiner* — Scott Getzow

(57) ABSTRACT

A method for diagnosing an implantable cardiac device including a plurality of implanted leads may include: monitoring a plurality of parameters associated with the plurality of implanted leads; detecting a change in one of the parameters; evaluating at least one of the other parameters upon detection of the change; and diagnosing a problem with the implantable cardiac device based on the detected change and the evaluation. A system for diagnosing an implantable cardiac device including a plurality of implanted leads may include an implantable pacing device and a processor. The processor may be configured to: monitor a plurality of parameters associated with the plurality of implanted leads; detect a change in one of the parameters; evaluating at least one of the other parameters upon detection of the change; and diagnose a problem with the implantable cardiac device based on the detected change and the evaluation.

20 Claims, 6 Drawing Sheets

| U.S. PATENT DOCUMENTS | | | | FOREIGN PATENT DOCUMENTS | | |
|---|---|---|---|---|---|---|
| 2003/0204215 A1 | 10/2003 | Gunderson et al. | WO | 03077822 A3 | 9/2003 |
| 2004/0064161 A1 | 4/2004 | Gunderson et al. | WO | 2006116430 A2 | 11/2006 |
| 2004/0162593 A1 | 8/2004 | Jorgenson et al. | WO | 2006116430 A3 | 11/2006 |
| 2005/0125041 A1 | 6/2005 | Min et al. | WO | 2006119131 A1 | 11/2006 |
| 2006/0247706 A1 | 11/2006 | Germanson et al. | WO | 2006119136 A1 | 11/2006 |

FIG. 6    500

| SENSING THRESHOLD AND/OR | CAPTURE THRESHOLD | BIPOLAR IMPEDANCE | PRESUMPTIVE DIAGNOSIS |
|---|---|---|---|
| DETERIORATION IN SIGNAL AMPLITUDE | ABRUPT RISE IN CAPTURE THRESHOLD | NORMAL | LEAD DISLODGEMENT |
| DETERIORATION IN SIGNAL AMPLITUDE | ABRUPT RISE IN CAPTURE THRESHOLD | LOW | INTERNAL INSULATION FAILURE |
| DETERIORATION IN SIGNAL AMPLITUDE | ABRUPT RISE IN CAPTURE THRESHOLD | HIGH | CONDUCTOR COIL FRACTURE |
| DETERIORATION IN SIGNAL AMPLITUDE | NORMAL CAPTURE THRESHOLD | NORMAL | CHANGE IN SIGNAL BUT STABLE AND NORMAL LEADS |
| CHANGE IN CONDUCTION INTERVAL BETWEEN TWO LEADS | CAPTURE THRESHOLD MEASURED INDEPENDENTLY ON BOTH LEADS. ABRUPT RISE IN CAPTURE THRESHOLD ON ONE LEAD | NORMAL | LEAD DISLODGEMENT ASSOCIATED WITH THE HIGHER THRESHOLD |
| CHANGE IN CONDUCTION INTERVAL BETWEEN TWO LEADS | CAPTURE THRESHOLD MEASURED INDEPENDENTLY ON BOTH LEADS. ABRUPT RISE IN CAPTURE THRESHOLD ON ONE LEAD | LOW | INTERNAL INSULATION FAILURE ON THE LEAD WITH THE HIGHER THRESHOLD AND LOW IMPEDANCE |
| CHANGE IN CONDUCTION INTERVAL BETWEEN TWO LEADS | CAPTURE THRESHOLD MEASURED INDEPENDENTLY ON BOTH LEADS. ABRUPT RISE IN CAPTURE THRESHOLD ON ONE LEAD | HIGH | CONDUCTOR COIL FRACTURE ON THE LEAD WITH THE HIGHER THRESHOLD |
| CHANGE IN MORPHOLOGY OF INTRINSIC SIGNAL | ABRUPT RISE IN CAPTURE THRESHOLD | NORMAL | LEAD DISLODGEMENT |
| CHANGE IN MORPHOLOGY OF INTRINSIC SIGNAL | ABRUPT RISE IN CAPTURE THRESHOLD | LOW | INTERNAL INSULATION FAILURE |
| CHANGE IN MORPHOLOGY OF INTRINSIC SIGNAL | ABRUPT RISE IN CAPTURE THRESHOLD | HIGH | CONDUCTOR COIL FRACTURE |
| INCREASE IN SIGNAL AMPLITUDE (BIPOLAR SENSING) | DECREASE OR NO CHANGE IN CAPTURE THRESHOLD | NORMAL | NORMAL |
| INCREASE IN SIGNAL AMPLITUDE (BIPOLAR SENSING) | INCREASE IN CAPTURE THRESHOLD (ASSOCIATED WITH LEAKAGE OF CURRENT) | NORMAL (UNLESS THERE IS A MASSIVE BREACH OF THE EXTERNAL INSULATION, THE IMPEDANCE WILL NOT CHANGE TO A DETECTABLE DEGREE) | FAILURE OF EXTERNAL INSULATION |

SYSTEMS AND METHODS FOR DIAGNOSING AN IMPLANTABLE DEVICE

FIELD OF THE INVENTION

The present invention relates to medical devices and methods. More specifically, the present invention relates to medical devices and methods of using such devices, particularly to diagnosis of potential problems with operation of such devices.

BACKGROUND OF THE INVENTION

Implantable cardiac devices have become increasingly sophisticated and more capable over time. The initial implantable cardiac devices were typically comprised of pacemakers, which provided electrical pacing pulses to the heart at a generally fixed rate. As the technology has developed, more advanced pacing systems have been implanted in patients, which, for example, are capable of providing pacing pulses to the heart only when the pacing system determines that the heart will not provide an intrinsic heart beat. Moreover, such advanced pacemakers are also able to adjust the pacing rate to accommodate different levels of physical activity and corresponding metabolic demand of the patient.

Typically, pacing systems are equipped with sensors, which provide signals that are used by the control unit of the pacing system to determine the pacing rate. Such sensors include activity sensors, such as an accelerometer, metabolic rate sensors, such as a minute ventilation sensor, electrical sensors, such as an impedance sensor, and pressure sensors.

Cardiac devices are also known to be able to perform automatic testing functions, such as threshold testing for automatic capture verification. Examples of known devices and methods include those described in U.S. Pat. Nos. 6,129,746; 6,243,606; 6,259,950; 6,263,244; 6,285,908; 6,295,471; 6,311,089; 6,366,812; 6,389,316; 6,408,210; 6,430,441; 6,477,417; 6,546,288; 6,584,354; 6,594,523; 6,618,622; 6,721,601; 6,766,197; 6,792,307; 6,925,326; and 6,934,587, each of which is incorporated by reference herein in its entirety.

Further, some cardiac devices are known to include lead impedance surveillance capabilities. For example, U.S. Pat. No. 7,031,773 to Levine et al., which is incorporated by reference herein in its entirety, describes a system in which an impedance measurement is triggered by a high capture threshold identified by an autocapture algorithm.

BRIEF SUMMARY

Embodiments described herein contemplate evaluating a plurality of parameters to diagnose a problem with an implantable cardiac device. Further, embodiments contemplate identifying and/or differentiating between different mechanical problems.

Embodiments of described herein contemplate a method for diagnosing an implantable cardiac device including a plurality of implanted leads. The method may comprise: monitoring a plurality of parameters associated with the plurality of implanted leads; detecting a change in one of the parameters; evaluating at least one of the other parameters upon detection of the change; and diagnosing a problem with the implantable cardiac device based on the detected change and the evaluation.

The method may also comprise providing a notification of the problem to an external device. Such notification may comprise notification of a dislodgement, an insulation breach or a conductor coil fracture.

In some embodiments, the plurality of parameters may include at least two of a timing interval between leads, signal amplitude(s), morphology of a signal, capture threshold and impedance.

In some embodiments, diagnosing the problem with the implantable cardiac device may comprise identifying dislodgement of one of the implanted leads. In some embodiments, diagnosing the problem with the implantable cardiac device may comprise identifying a mechanical problem other than dislodgement of one of the implanted leads. In some embodiments, diagnosing the problem with the implantable cardiac device may comprise differentiating dislodgement of one of the implanted leads from a different mechanical problem.

In some embodiments, diagnosing the problem with the implantable cardiac device may comprise accessing a matrix of parameter changes, parameter evaluation values, and diagnoses associated with combinations of the parameter changes and parameter evaluation values.

Embodiments disclosed herein contemplate a system that is configured to diagnose an implantable cardiac device including a plurality of implanted leads. The system may comprise an implantable pacing device and a processor. The processor may be configured to: monitor a plurality of parameters associated with the plurality of implanted leads; detect a change in one of the parameters; evaluating at least one of the other parameters upon detection of the change; and diagnose a problem with the implantable cardiac device based on the detected change and the evaluation.

In some embodiments, the system may include communication circuitry coupled to the processor and configured to provide a notification of the problem to an external device, such as a dislodgement of an implanted lead, an insulation breach of a lead and/or a conductor coil fracture of a lead.

In some embodiments, the processor may be configured to monitor and evaluate at least two of a timing interval between leads, signal amplitude(s), morphology of a signal, capture threshold and impedance. In some embodiments, the processor may be configured to identify dislodgement of one of the implanted leads. In some embodiments, the processor may be configured to identify a mechanical problem other than dislodgement of one of the implanted leads, such as an insulation breach of a lead and/or a conductor coil fracture of a lead. In some embodiments, the processor may be configured to differentiate dislodgement of one of the implanted leads from a different mechanical problem.

Some embodiments may further comprise a storage element coupled to the processor. The storage element may store a matrix of parameter changes, parameter evaluation values, and diagnoses associated with combinations of the parameter changes and parameter evaluation values. In such embodiments, the processor may be configured to diagnose the problem with the implantable cardiac device by accessing the matrix.

While multiple embodiments are disclosed, still other embodiments will become apparent to those skilled in the art from the following detailed description, which shows and describes illustrative embodiments. As will be realized, the details provided herein are capable of modifications in various aspects, all without departing form the spirit and scope of the present invention. Accordingly, the drawings and detailed description are to be regarded as illustrative in nature and not restrictive.

BRIEF DESCRIPTION OF THE DRAWINGS

FIG. 6 is an illustration of a matrix that may be employed in the diagnostic feature of the implantable device of FIG. 2.

DETAILED DESCRIPTION

The following description is of embodiments presently contemplated for practicing various aspects of the invention. This description is not to be taken in a limiting sense but is made merely for the purpose of describing general principles. The scope of the invention should be ascertained with reference to the issued claims. In the description that follows, like numerals or reference designators will be used to refer to like parts or elements throughout.

Embodiments are described herein in relation to a cardiac stimulation device capable of delivering precisely ordered stimulation pulses to multiple chambers of the heart, referred to herein as multi-chamber stimulation, or to multiple sites within a chamber of the heart, referred to herein as multi-site stimulation. The stimulation device is intended for use in patients suffering from hemodynamic dysfunction and/or electrical abnormalities within the heart, which may or may not be accompanied by conduction disorders. Precisely controlled stimulation at multiple sites or in multiple chambers is provided to intentionally make use of the pacing function of the heart to improve cardiac hemodynamics by re-coordinating heart chamber contractions and/or preventing further electrical problems such as arrhythmogenic depolarizations from occurring. Thus, the cardiac stimulation device is capable of delivering at least low-voltage stimulation pulses to multiple stimulation sites for providing pacing therapy, and may include high-voltage stimulation shocks for providing cardioversion therapy and defibrillation therapy.

The disclosed devices and methods are directed at diagnosing potential problems associated with the implantable device system. In particular, the disclosed devices and methods are directed at diagnosing dislodgement of an implanted lead. Further, the disclosed devices and methods are directed at diagnosing and differentiating various mechanical problems including lead dislodgement. Thus, the methods described herein may be incorporated in any such cardiac stimulation device.

Figure 1:
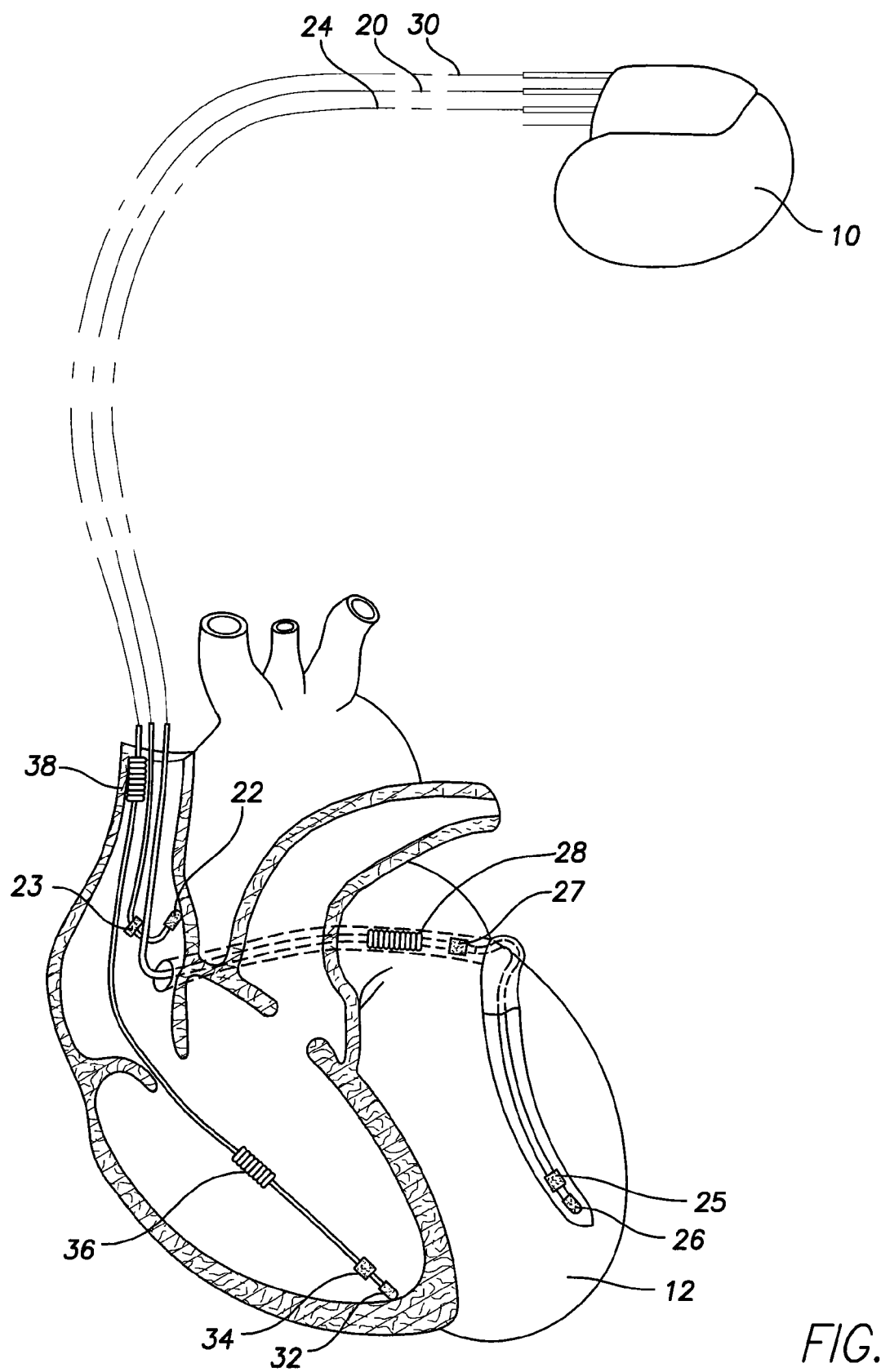
FIG. 1 is a simplified, partly cutaway view of a patient's heart and illustrating an implantable stimulation device in electrical communication with at least three leads implanted into the heart for delivering multi-chamber stimulation and shock therapy.
Figure 2:
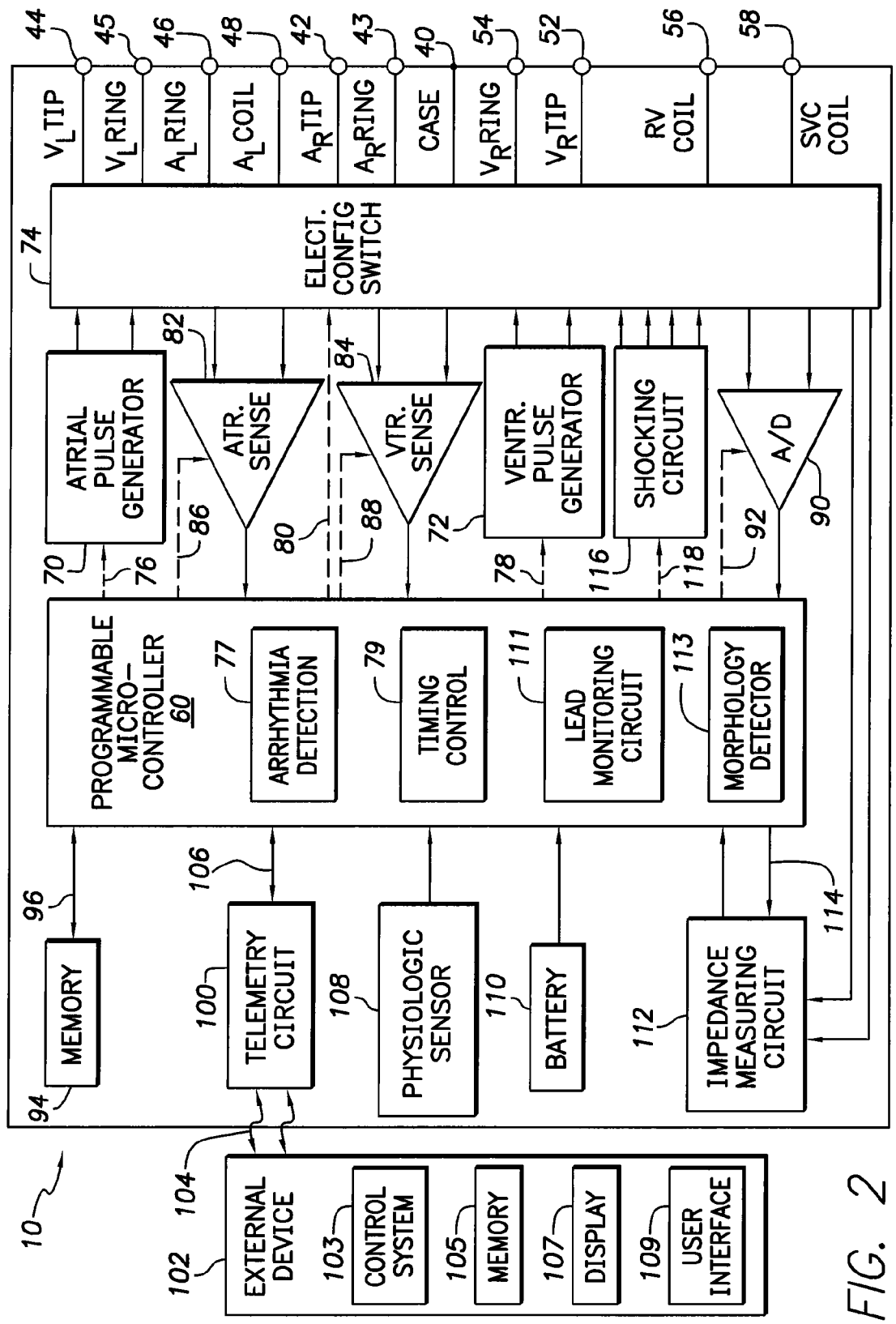
FIG. 2 is a functional block diagram of the multi-chamber implantable stimulation device of FIG. 1, illustrating the basic elements that provide pacing stimulation, cardioversion, and defibrillation in four chambers of the heart.

A general cardiac stimulation device will thus be described in conjunction with FIGS. 1 and 2, in which the diagnostic methods described herein may be implemented. It should be understood, however, that numerous variations of such a device in which the methods may be implemented. Similarly, a general telemetry/programmer device will be described in conjunction with FIG. 3. The telemetry/programmer device may be used to program and/or obtain data from the cardiac stimulation device. It should be understood, however, that numerous variations of telemetry/programmer devices exist that may be used.

FIG. 1 illustrates a stimulation device 10 in electrical communication with a patient's heart 12 by way of three leads 20, 24 and 30 suitable for delivering multi-chamber stimulation and shock therapy. To sense right atrial cardiac signals and to provide right atrial chamber stimulation therapy, the stimulation device 10 is coupled to an implantable right atrial lead 20 having at least an atrial tip electrode 22, which typically is implanted in the patient's right atrial appendage. The right atrial lead 20 may also have a right atrial ring electrode 23 to allow bipolar stimulation or sensing in combination with the right atrial tip electrode 22.

To sense the left atrial and ventricular cardiac signals and to provide left-chamber stimulation therapy, the stimulation device 10 is coupled to a "coronary sinus" lead 24 designed for placement in the "coronary sinus region" via the coronary sinus ostium so as to place a distal electrode adjacent to the left ventricle and additional electrode(s) adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to receive atrial and ventricular cardiac signals and to deliver: left ventricular pacing therapy using at least a left ventricular tip electrode 26, optional left atrial pacing therapy using at least a left atrial ring electrode 27, and optional shocking therapy using at least a left atrial coil electrode 28. In an alternative embodiment, the coronary sinus lead 24 may also include a left ventricular ring electrode 25.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle. It should be understood that shocking coils may not be included in the leads, and that non-shocking electrodes may also allow for the measurements discussed herein.

FIG. 2 illustrates a simplified block diagram of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The stimulation device 10 includes a housing 40 which is often referred to as "can", "case" or "case electrode", and which may be programmably selected to act as the return electrode for all "unipolar" modes. The housing 40 may further be used as a return electrode alone or in combination with one or more of the coil electrodes 28, 36, or 38, for shocking purposes. The housing 40 further includes a connector having a plurality of terminals, 42, 44, 45, 46, 48, 52, 54, 56, and 58 (shown schematically and, for convenience, the names of the electrodes to which they are connected are shown next to the terminals). As such, to achieve right atrial sensing and stimulation, the connector includes at least a right atrial tip terminal ($A_R$ TIP) 42 adapted for connection to the atrial (AR) tip electrode 22. The connector may also include a right atrial ring terminal ($A_R$ RING) 43 for connection to the atrial ring electrode 23, and a left ventricular ring ($V_L$ RING) 45 for connection to the left ventricular ring electrode 25.

To achieve left chamber sensing, pacing, and shocking, the connector includes at least a left ventricular tip terminal ($V_L$ TIP) 44, a left atrial ring terminal ($A_L$ RING) 46, and a left atrial shocking coil terminal ($A_L$ COIL) 48, which are adapted for connection to the left ventricular tip electrode 26, the left atrial ring electrode 27, and the left atrial coil electrode 28, respectively.

To support right ventricular sensing, pacing and shocking, the connector further includes a right ventricular tip terminal ($V_R$ TIP) 52, a right ventricular ring terminal ($V_R$ RING) 54, a right ventricular shocking coil terminal (RV COIL) 56, and an SVC shocking coil terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 that controls the various modes of stimulation therapy. The microcontroller 60 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. Any suitable microcontroller 60 may be used that carries out the functions described herein.

Representative types of control circuitry that may be used with the present invention include the microprocessor-based control system of U.S. Pat. No. 4,940,052 to Mann et al. al. For a more detailed description of the various timing intervals used within the stimulation device and their inter-relationship, reference is made to U.S. Pat. No. 4,788,980 (Mann et. al). Each of these references is incorporated by reference herein in its entirety.

FIG. 2 illustrates an atrial pulse generator 70 and a ventricular pulse generator 72 that generate stimulation pulses for delivery by the right atrial lead 20, the right ventricular lead 30, and/or the coronary sinus lead 24 via an electrode configuration switch 74. It is understood that to provide stimulation therapy in each of the four chambers of the heart, the atrial and ventricular pulse generators, 70 and 72, may include dedicated, independent pulse generators, multiplexed pulse generators, or shared pulse generators. The atrial pulse generator 70 and the ventricular pulse generator 72 are controlled by the microcontroller 60 via appropriate control signals 76 and 78, respectively, to trigger or inhibit the stimulation pulses.

It should be understood that the electrode configuration switch 74 illustrated in FIG. 2 may allow various electrode combinations to be used for stimulation and/or sensing. Thus, various configurations may be defined to implement the diagnostic feature described herein.

The microcontroller 60 further includes timing control circuitry 79, which is used to control the timing of such stimulation pulses (e.g., pacing rate, atrial-ventricular (AV) delay, atrial interconduction (A-A) delay, or ventricular interconduction (V-V) delay, etc.), as well as to keep track of the timing of refractory periods, blanking intervals, noise detection windows, evoked response detection windows, alert intervals, marker channel timing, etc.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, cross-chamber, etc.) by selectively closing the appropriate combination of switches.

Atrial sensing circuits (ATR. SENSE) 82 and ventricular sensing circuits (VTR. SENSE) 84 may also be selectively coupled to the right atrial lead 20, coronary sinus lead 24 which will detect left ventricular activity, and the right ventricular lead 30, through the switch 74, for detecting the presence of cardiac activity in each of the four chambers of the heart. Accordingly, the atrial and ventricular sensing circuits 82 and 84 may include dedicated sense amplifiers, multiplexed amplifiers, or shared amplifiers. The switch 74 determines the "sensing polarity" of the cardiac signal by selectively closing the appropriate switches. In this way, the clinician may program the sensing polarity independent of the stimulation polarity.

Stimulation during pacing may be performed in a bipolar mode in devices combining pacing and cardioversion/defibrillation functions because unipolar stimulation may interfere with arrhythmia detection. Hence, in one embodiment, the switch bank 74 is configured such that: right atrial pacing and sensing is performed in a bipolar fashion between the right atrial tip electrode 22 and right atrial ring electrode 23; right ventricular pacing and sensing is performed in a bipolar fashion between right ventricular tip electrode 32 and right ventricular ring electrode 34; and left ventricular pacing and sensing is performed in a bipolar fashion between coronary sinus tip electrode 26 and the coronary sinus ring electrode 27. Right ventricular sensing may alternatively be configured between the right ventricular coil electrode 36 and the right ventricular ring electrode 34. Bipolar sensing may also be achieved using an integrated bipolar lead wherein the right ventricular coil electrode 36 and right ventricular ring electrode 34 are electrically coupled within the right ventricular lead body 30. Bipolar sensing is then performed between the right ventricular tip electrode 32 and the coupled right ventricular coil electrode 36 and right ventricular ring electrode 34. Any electrode combination that allows acceptable stimulation and sensing thresholds may be used. By employing the right ventricular coil electrode 36, possibly in combination with right ventricular ring electrode 34, the electrode surface during sensing is increased, advantageously reducing the effects of lead polarization. Other techniques of reducing lead polarization such as titanium nitride coating may also be used to improve the operation.

Each sensing circuit, 82 and 84, preferably employs one or more low power, precision amplifiers with programmable gain and automatic gain or sensitivity control, bandpass filtering, and a threshold detection circuit, to selectively sense the cardiac signal of interest. The automatic sensitivity control enables the stimulation device 10 to deal effectively with the difficult problem of sensing the low amplitude signal characteristics of atrial or ventricular fibrillation.

The outputs of the atrial and ventricular sensing circuits, 82 and 84, are connected to the microcontroller 60 for triggering or inhibiting the atrial and ventricular pulse generators 70 and 72, respectively, in a demand fashion, in response to the absence or presence of cardiac activity in the appropriate chambers of the heart. The atrial and ventricular sensing circuits 82 and 84, in turn, receive control signals over signal lines 86 and 88 from the microcontroller 60, for controlling the gain, threshold, polarization charge removal circuitry, and the timing of any blocking circuitry coupled to the inputs of the atrial and ventricular sensing circuits 82 and 84.

For arrhythmia detection, the stimulation device 10 utilizes the atrial and ventricular sensing circuits 82 and 84 to sense cardiac signals for determining whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (e.g., bradycardia, normal, low rate VT, high rate VT, and fibrillation rate zones) and various other characteristics (e.g., sudden onset, stability, physiologic sensors, and morphology, etc.), to determine the type of remedial therapy that is needed (e.g., bradycardia pacing, anti-tachycardia stimulation, cardioversion shocks or defibrillation shocks, collectively referred to as "tiered therapy").

Cardiac signals are also applied to the inputs of a data acquisition system 90, which is depicted as an analog-to-digital (A/D) converter for simplicity of illustration. The data acquisition system 90 is configured to acquire intracardiac electrogram (EGM) signals, convert the raw analog data into digital signals, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

Advantageously, the data acquisition system 90 may be coupled to the microcontroller 60 or another detection circuitry, for detecting an evoked response from the heart 12 in response to an applied stimulus, thereby aiding in the detection of "capture." The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on the amplitude, determines if capture has occurred. The implementation of an exemplary capture detection circuitry and algorithm is described, for example, in U.S. Pat. No. 4,969,467 to Callaghan et al., which is incorporated by reference herein in its entirety.

The microcontroller 60 is further coupled to a memory 94 by a suitable data/address bus 96, wherein the programmable operating parameters used by the microcontroller 60 are stored and modified, as required, to customize the operation of the stimulation device 10 to suit the needs of a particular patient. Such operating parameters define, for example, stimulation pulse amplitude, pulse duration, electrode polarity, rate, sensitivity, automatic features, arrhythmia detection criteria, and the amplitude, waveshape and vector of each stimulation pulse to be delivered to the patient's heart 12 within each respective tier of therapy. A feature is the ability to sense and store a relatively large amount of data (e.g., from the data acquisition system 90), which data may then be used for subsequent analysis to guide the programming of the device. In a preferred embodiment, data resulting from periodic threshold tests are written to memory 94. The threshold measurement and the time and date at which it was made are stored in memory 94 so that changes in threshold over time may be graphically displayed on an external device 102, such as a programmer with an LCD display, after being downloaded via telemetry circuit 100 and communication link 104.

Advantageously, the operating parameters of the stimulation device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the stimulation device 10 (as contained in the microcontroller 60 or memory 94) to be sent to the external device 102 through the established communication link 104. In a preferred embodiment, with a telemetry wand or any other suitable means of communicating with the stimulation device 10, an evoked response sensitivity test can be performed according to a control program located in external device 102, in this case a programmer. The methods of an evoked response sensitivity test will be described in detail in conjunction with FIG. 3.

The stimulation device 10 may further include a physiologic sensor 108, commonly referred to as a "rate-responsive" sensor because it is typically used to adjust stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various stimulation parameters (such as rate, AV Delay, V-V Delay, etc.) at which the atrial and ventricular pulse generators 70 and 72 generate stimulation pulses.

The stimulation device 10 additionally includes a power source such as a battery 110 that provides operating power to all the circuits shown in FIG. 2. For the stimulation device 10, which employs shocking therapy, the battery 110 must be capable of operating at low current drains for long periods of time, preferably less than 10 microA, and also be capable of providing high-current pulses when the patient requires a shock pulse, preferably, in excess of 2 A, at voltages above 2 V, for periods of 10 seconds or more. The battery 110 preferably has a predictable discharge characteristic so that elective replacement time can be detected.

As further illustrated in FIG. 2, the stimulation device 10 is shown to include an impedance measuring circuit 112 that is enabled by the microcontroller 60 via a control signal 114.

In the case that it is a primary function of the stimulation device 10 to operate as an implantable cardioverter/defibrillator (ICD) device, it must detect the occurrence of an arrhythmia (via the arrhythmia detector 77), and automatically apply an appropriate electrical stimulation or shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5-10 Joules), or high (11 to 40 Joules) energy, as controlled by the microcontroller 60. Such shocking pulses are applied to the patient's heart through at least two shocking electrodes, and as shown in this embodiment, selected from the left atrial coil electrode 28, the RV coil electrode 36, and/or the SVC coil electrode 38 (FIG. 1).

As noted above, the housing 40 may act as an active electrode in combination with the RV coil electrode 36, or as part of a split electrical vector using the SVC coil electrode 38 or the left atrial coil electrode 28 (i.e., using the RV coil electrode 36 as a common electrode).

Cardioversion shocks are generally considered to be of low to moderate energy level (so as to minimize pain felt by the patient), and/or synchronized with an R-wave and pertaining to the treatment of tachycardia. Defibrillation shocks are generally of moderate to high energy level (i.e., corresponding to thresholds in the range of 5-40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
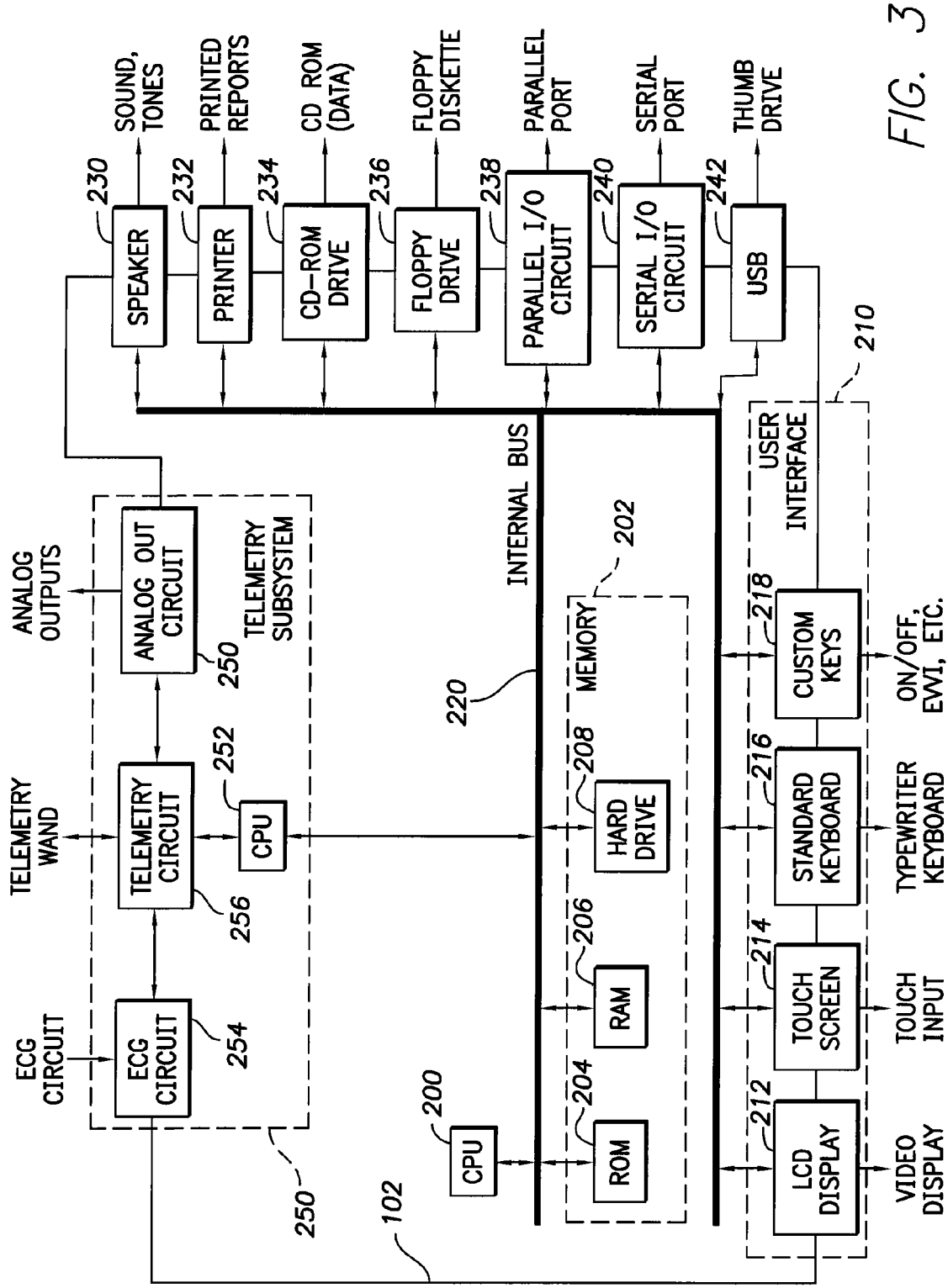
FIG. 3 is a block diagram illustrating the basic elements of an external device that may send and receive commands or data through telemetric communication with the implantable device of FIG. 2.

FIG. 3 illustrates a simplified block diagram of the external programming device 102 that communicates with device 10 through a telemetry circuit 100. The external device 102 includes a central processing unit (CPU) 200 that controls the operations carried out by the external device 102, such as programming the operating parameters of device 10 or carrying out various testing or diagnostic functions. Testing and diagnostic functions preferably include evoked response sensitivity testing, and may also include algorithms or methods for non-invasive programmed stimulation for arrhythmia induction, arrhythmia detection and termination testing, threshold testing, lead impedance measurements, etc.

CPU 200 is in communication with a memory (or data storage) 202 via an internal bus 220. The memory 202 may include a read-only memory (ROM) 204, a random access memory (RAM) 206, and hard drive 208. Operating parameters and algorithms controlling the programming and testing functions carried out by the external device 102 may be stored in memory 202 and accessed by CPU 200.

External device 102 is equipped with a user interface 210 that allows connection to an LCD display 212, a touch screen 214, a keyboard 216, and custom keys 218 that control a specific function or deliver a specific command automatically. Each component of the user interface 210 is also in communication with the CPU 200 and memory 202 via the internal bus 220 to allow user input, such as programming commands delivered using the touch screen 214, keyboard 216, or custom keys 218, to be received by the CPU 200 and/or stored in memory 202.

Programming selections made by a user and results of programming or testing operations may be displayed on the video display 212. Messages relating to the success of the programming command, recommended programmed settings, or warnings to the user regarding selected parameters may also be displayed on the video display 212.

The CPU 200 and memory 202 are also in communication with various input/output interfaces via the internal bus 220 that may include: a speaker 230 for delivering sounds or tones during the programming procedures; a printer 232 for printing results of programming or testing operations; a CD-ROM drive 234 and floppy drive 236 to which data from testing or programming operations may be written; and a parallel input/output port 238 and a serial input/output port 240 and/or a USB port 242 to allow connection to auxiliary equipment.

The external device 102 is further equipped with a telemetry subsystem 250. The telemetry subsystem 250 includes a central processing unit (CPU) 252 for controlling the transfer of data between the external device 102 and the implanted device 10. Thus, the telemetry CPU 252 is in communication with the internal bus 220 so that data may be transferred between the telemetry subsystem 250 the CPU 200, memory 202, user interface 210, and other input/output interfaces, 230, 232, 234, 236, 238, 240 and 242.

The telemetry CPU 252 is connected to at least three interfaces which facilitate the receipt or transmission of data. An ECG circuit interface 254 allows connection to surface ECG leads for collecting a patient's ECG. The ECG may be displayed in real time on the video display 212. A telemetry circuit interface 256 allows connection to a telemetry wand that is placed over the implanted device 10, or other means of communicating with the implanted device 10, for receiving or sending data such as cardiac signal data stored in the memory 94 of device 10 or programmed operating parameters received at the user interface 210. An analog output circuit interface 258 allows connection to an analog output port to a remote printer or data recording system such as a hospital based electronic record.

A system that is configured to diagnose the device 10 may be incorporated into the device 10, and may include the device itself. It should be understood however, that other configurations are possible, such as a system comprising the device 10 and elements external to the device 10. With respect to FIG. 2, the system is described as being incorporated into the device 10.

The microcontroller 60 or another processor (not shown) may be configured to monitor a plurality of parameters associated with the plurality of implanted leads 20, 24 and 30. It should be noted that such monitoring may be of the leads 20, 24 and 30 or of the various electrodes thereof. As such, in the following description, it should be understood that reference to "leads" encompasses individual electrodes as well, although not explicitly stated for the sake of simplicity. The electrodes are the exposed metal, for example, at the ends of the leads that make contact with the cardiac tissue and may serve to detect electrical signals from the respective locations as well as to stimulate the respective locations. As used in this description, the "lead" will be used to refer to all components of the lead, including the terminal pin connecting the lead to the pulse generator, the lead body consisting of one or more wires covered by an insulating material, and the electrodes connected with the one or more wires.

For example, the device 10 may include a morphology detector 113 and circuitry for lead monitoring 111, which may be included in the microcontroller 60 as modules, applications, routines, etc. Various techniques for monitoring leads and/or detecting the morphology of a signal are known, and may be incorporated in the morphology detector 113 and circuitry 111. In particular, morphology detection (MD) is well known in the art. Particular MD algorithms may be employed, such as those described in U.S. Pat. Nos. 6,928,362 and 7,149,569, which are incorporated herein by reference in their entirety.

In particular, the morphology detector 113 may be configured to detect a change in the morphology of a signal by comparing the signal to an acquired template. The template may be acquired, for example, during normal operation of the device 10 and stored in the memory 94. Knowing that signals from the same source may change with time, the current MD algorithm contemplated, such as those mentioned above, may be programmed to automatically reassess template morphology daily, or less frequently, as appropriate or desired. In addition, as there may be subtle variations in the template, a correct match may be set at 60-70% of the stored template with a further requirement that there be a match in X out of Y events to confirm a match. Similar criteria may be applied to the techniques disclosed herein. Both the number of correct matches and the degree of match may be programmable options. For example, in a currently available MD algorithm, such an approach is used to differentiate a supraventricular tachycardia from ventricular tachycardia, and thus the stimulation device may only be enabled when the ventricular rate is sufficiently fast to fall within a VT rate zone. In embodiments, the automatic periodic assessment of the morphology template may occur with the patient at rest. Further, in embodiments described herein, the morphology template may be acquired at normal heart rates. A change in the morphology of a signal may be detected or determined by the morphology detector 113 and may indicate that one or both leads is partially or totally dislodged, or that some other mechanical problem exists, such as a breach of the insulation of a lead and/or a fractured conduction coil.

The lead monitoring circuit 111 may be configured to determine a change in conduction timing intervals between leads. For example, a stable interval between conduction in two leads in different locations may exist when both leads are properly secured or lodged in cardiac tissue. One example is right ventricle and left ventricle leads (electrodes). The stable interval need not be a discrete value, but may be a suitable range based on conduction intervals measured during normal operation of the device 10. For example, in individuals with a normal duration QRS complex, the interval between right ventricular activation and left ventricular activation may be 40 to 60 ms, whereas in individuals with an intraventricular conduction defect, commonly called a bundle branch block, the interval between right ventricular activation and left ventricular activation may be 120 ms or longer. A change in conduction timing intervals between leads when the intrinsic rhythm is present may be detected or determined by the lead monitoring circuit 111 and may indicate that one or both leads is partially or totally dislodged, or that some other mechanical problem exists as discussed above. As described in U.S. Patent Application Publication No. 2005/0125041, which is incorporated herein by reference in its entirety, an optimization algorithm, for optimizing both atrioventricular and ventricular-ventricular timing in CRT systems, may run through a series of programming changes to pace in the atrium and measure the time to depolarization of the ventricle, to pace in one ventricular chamber to measure conduction to the other ventricular chamber, and vice versa. Thus, in embodiments described herein, this capability may be performed automatically, for example, depending on appropriate triggers.

Other changes may indicate partial or total dislodgement of a lead or other mechanical problem(s) with the lead as well. For example, an abrupt change in signal amplitude, fluctuations in signal amplitude(s), a change in the capture threshold and/or a "high output mode" in association with an autocapture process or algorithm may also be detected. An autocapture algorithm may be configured to automatically assess the capture threshold. For example, the methods described in U.S. Pat. No. 6,950,704 or the methods described in U.S. Pat. Nos. 5,184,615 and 6,731,985, each of which is incorporated herein by reference in its entirety, may be used. In such algorithms, the system may monitor capture on the ventricular channel on a beat-by-beat basis. If the system fails to detect the depolarization associated with the pacing stimulus, the system may diagnose a loss of capture and may deliver a significantly higher output pulse, for example, 4.5 or 5.0 volts, approximately 100 ms after the primary pulse that was interpreted by the system as a loss of capture. If loss of capture is demonstrated on the next primary pulse, the algorithm may progressively increase the voltage on the primary pulse until there is capture on two consecutive pulses. Thereafter, the system may reassess the capture threshold. If capture cannot be confirmed or the threshold is very high, the system may default to a "high output mode" such as 4.5 volts or 5.0 volts depending on the particular device.

Because theses changes may indicate various mechanical problems, further monitoring, detection or measurement may be needed to correctly diagnose the problem. Thus, when a change in one of the parameters being monitored (or, in some embodiments; a single parameter may be monitored) is detected, the microcontroller 60 may be triggered to evaluate one or more other parameters. The microcontroller 60 may be triggered to detect or measure other parameter(s) to evaluate, or may be triggered to evaluate parameter(s) being monitored, for example, using the current value(s) of the parameter(s) at the time the change is detected. The microcontroller 60 may diagnose the problem with the implantable cardiac device based on the detected change and the evaluation.

For example, once a change in a monitored parameter is detected, another parameter, such as impedance of the lead or leads, may be detected or measured. If the impedance is within a normal range (i.e., the impedance is within a range of values that exist during normal or proper operation of the device 10), then the problem may be determined to be a partial or total dislodgement of the lead. Normally, the impedance may range between 200 ohms and 2000 ohms, depending on the design of the lead. It may be desirable not to have any individual lead vary by more than 300 ohms on either side. Hence, if on initial interrogation, the bipolar lead impedance is 650 ohms, one would not expect that the lead impedance would go below 350 ohms or above 950 ohms. For lead impedance monitoring, absolute ranges may be selected, such as below 200 ohms or above 2000 ohms, and if such an impedance is encountered, the system may trigger a patient notification system and/or revert from bipolar stimulation to unipolar stimulation.

A marked drop or rise in impedance, such that the measured impedance is below or above the normal range of impedance values, may indicate different mechanical problems, specifically a problem with the insulation of the lead (drop in impedance) or an open circuit (rise in impedance), such as a broken conduction coil. Thus, by evaluating another parameter such as the impedance when a change is detected may allow the particular problem to be diagnosed or identified.

Triggering of an impedance measurement, for example, based on an autocapture assessment, is disclosed in the incorporated U.S. Pat. No. 7,031,733 ("the '733 Patent"). It should be understood from the foregoing that the approach of triggering of an impedance measurement and comparing the measurement to a given range as taught in the '733 Patent may be modified as needed to carry out the approach disclosed herein.

Thus, in general, the microcontroller 60 may be configured to monitor one or more parameters and to evaluate one or more parameters when a change in one of the parameters is detected. The system, as part of the microcontroller 60 or separate therefrom, may include any appropriate circuitry, sensors, modules and/or program code to monitor, detect and/or measure, etc. the desired parameters. By evaluating a parameter other than the parameter in which a change is detected, a particular mechanical problem may be diagnosed and/or identified. In other words, the approach described herein allows differentiation between different mechanical problems.

When a change in a parameter is detected and/or a problem is diagnosed, the patient associated with the device 10 and/or the doctor or hospital may be notified. Such notification may be physical, such as an electric pulse that differs from normal operation of the device, an audible sound, such as an alarm, a vibratory motor, and/or a wired or wireless transmission of a signal or data. For example, notification may be to a wireless communication device, such as a cell phone or personal digital assistant (PDA), or to a remote monitoring system, such as described in copending U.S. patent application Ser. No. 11/972,065, filed Jan. 10, 2008 and entitled "Communication Device, Communication System and Communication Method for an Implantable Medical Device." In some embodiments, the external device 102 in FIG. 2 or as illustrated in FIG. 3 may receive the notification from the device 10. Alternatively or additionally, in some embodiments, the device 10 may be configured to vibrate and/or generate an audible alert to notify the patient.

Because the approach described herein allows differentiation between mechanical problems, the notification may indicate the type of mechanical problem that has occurred, such as a dislodgement, an insulation breach or a conductor coil fracture. Further, the notification may include an indication of the severity of the mechanical problem, for example, based on the variance of a parameter from a normal value or range. For example, a developing lead fracture, such as a fracture of individual filars in the lead, may result in a significant increase in the lead impedance measurement of more than 300 ohms from the baseline measurements (such as going from 650 ohms to 1300 ohms), but still not exceed the absolute upper limit of 2000 ohms. As such, this will not be as critical as total disruption of the lead, and may allow for an elective rather than emergent management. As such, the intensity of the patient notification may vary.

Figure 4:
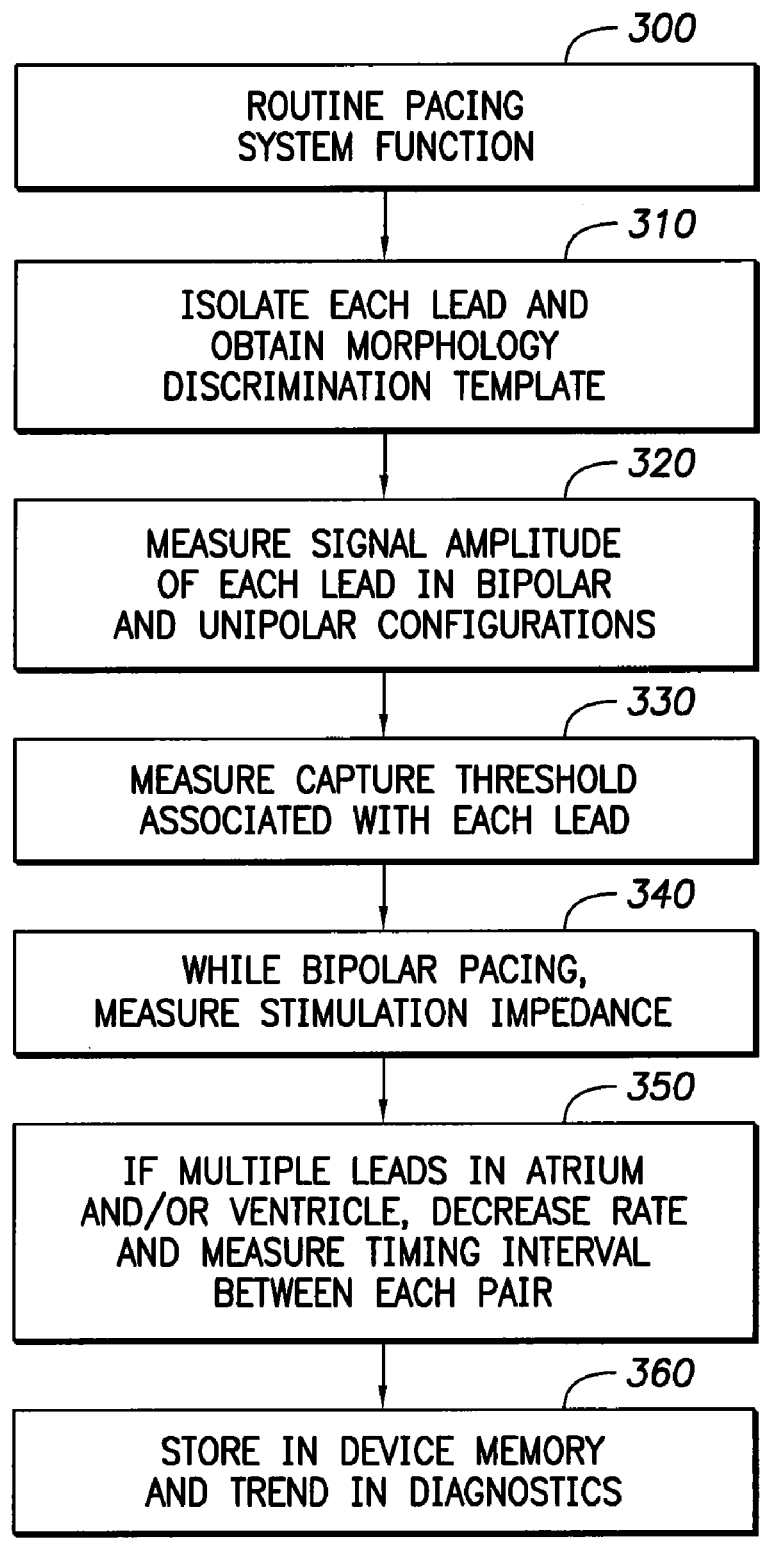
FIG. 4 is a process flow chart illustrating an overview of initial operations that may be included for a diagnostic feature of the implantable device of FIG. 2.
Figure 5:
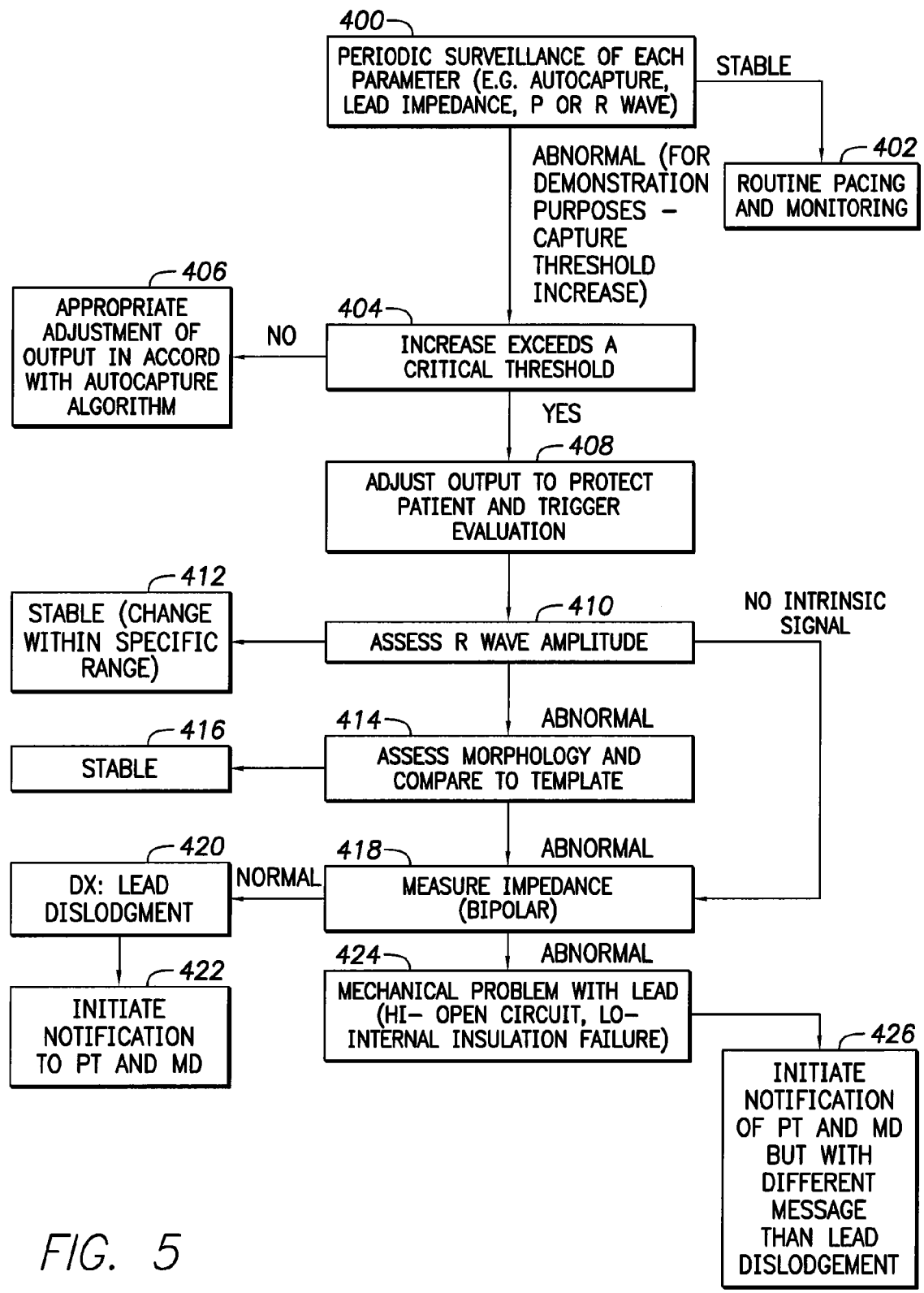
FIG. 5 is a process flow chart illustrating an overview of operations that may be included in the diagnostic feature of the implantable device of FIG. 2.

In FIGS. 4 and 5, flow charts are shown describing an overview of operations implemented in one embodiment of the implanted device 10 and external device 102. In these flow charts, the various algorithmic steps are summarized in individual "blocks". Such blocks describe specific actions or decisions that may be made or carried out as the algorithm proceeds. Where a microcontroller (a controller or an equivalent device) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

An initialization algorithm is represented in FIG. 4. This process may be implemented to "set up" the system for diagnosing the device 10. It should be understood that suitable hardware and/or software may be included in the device 10 or separate from the device 10 to carry out the various operations described. It should also be understood that the elements shown in FIG. 2 are only an example and not limiting.

The device 10 may be operating normally and may perform a routine pacing function [BLOCK 300]. Each lead may be isolated so that a morphology discrimination template may be obtained [BLOCK 310]. As discussed above, this may involve individually sensing the signal output by each lead to establish a template for each lead. Further, this may involve temporarily and automatically programming of the system that varies from the base programmed parameters to allow the measurement to be made. For example, if there is ventricular pacing in a biventricular pacing system, pacing from the right ventricular (RV) lead will allow measurements to be made with respect to the conduction time to the left ventricular (LV) lead as well as the morphology at the LV lead. The same may occur when pacing in the LV lead, allowing for measurement of the conduction time to the RV lead and the morphology of the RV lead depolarization in response to stimulation in the LV lead. Presuming that the AV nodal conduction is intact, the system may switch temporarily to single chamber atrial pacing to measure the conduction time to the RV lead and the RV morphology and perform similar measurements with respect to the LV lead. These various measurements may be stored, for example, in the pulse generator, for future reference.

The signal amplitude of each lead may be measured in both bipolar and unipolar configurations [BLOCK 320] to determine a reference value or range of values of amplitude for each lead in each configuration. The reference value or range of values may be used to detect changes or fluctuations in amplitude(s), as discussed above. The degree of change will be a programmable value cited as either a percentage of the baseline value or an absolute decrease or increase in signal amplitude in that signal amplitudes are known to vary. The signal amplitude may be measured over a series of consecutive cycles to define the range. A subsequent measurement that exceeds that range, either by a percentage of the mean value and/or an absolute amount, may signify a significant change for triggering a notification and/or an evaluation of another parameter, as discussed herein.

The capture threshold for each lead may also be measured [BLOCK 330]. As capture thresholds may wax and wane during the course of the day. Capture thresholds may also progressively increase with metabolic abnormalities, drug effects or maturation of the lead-tissue interface. The capture threshold may also decrease over a progressive period of time. As such, slow progressive changes may not warrant concern unless they are massive, such as exceeding the high output mode available in the device. An abrupt change in the capture threshold by more than three or four programming steps may indicate a significant change warranting evaluation of the lead status as discussed herein.

During bipolar pacing by the device 10, the stimulation impedance may be measured [BLOCK 340]. Further, when the device 10 includes multiple leads in the atrium and/or in the ventricle, the conduction timing interval between each pair of leads may be measured [BLOCK 350]. The degree of variation in conduction timing intervals that signifies a significant problem may be a programmable value determined by the doctor of medical technician, but may have a default value of 50 ms, for example. If the lead has dislodged, the change in conduction interval may also likely be associated with a change in capture threshold and/or morphology.

As each of the foregoing values or ranges is measured or determined, in any particular order, they may be stored in the memory 94 of the device 10 [BLOCK 360], for example. Thus, the values or ranges may be available to the microcontroller 60 for diagnostics once the initializing algorithm is completed.

The device 10 may be configured to execute such an algorithm upon initial set up. It should be understood that periodic or user-initiated updates may be implemented to run the algorithm after initial set up. Further, the individual operations may be performed independently from each other, for example, according to different algorithms. Thus, only algorithms for parameters needing updating may be performed. Moreover, it should be understood that the values or ranges may be determined during normal operation of the device 10 without necessarily performing a particular algorithm to initiate measurement.

A diagnostic algorithm is represented in FIG. 5. This process may be implemented to diagnose the device 10 during its operation. As discussed above with respect to FIG. 4, it should be understood that suitable hardware and/or software may be included in the device 10 or separate from the device 10 and that the elements shown in FIG. 2 are only an example and not limiting.

The diagnostic algorithm may periodically or continuously monitor each of a plurality of desired parameters [BLOCK 400]. Alternatively or additionally, the plurality of desired parameters may be checked by a user, such as a physician, as appropriate or desired. If all of the monitored/checked parameters are stable, that is, do not exhibit a change, fluctuation or difference from an associated reference value, then the device 10 may perform routine pacing and monitoring [BLOCK 402] as appropriate to the patient's condition.

If any of the monitored/checked parameters is abnormal, for example, the capture threshold increases, a determination of whether the increase exceeds a critical value may be made [BLOCK 404]. If not, then the output of the device 10 may be adjusted accordingly using the autocapture algorithm [BLOCK 406].

However, if the increase exceeds the critical threshold, the output may be adjusted to protect the patient and an evaluation of one or more other parameters may be triggered [BLOCK 408]. The other parameter(s) to be evaluated may include signal amplitude [BLOCK 410], signal morphology [BLOCK 414], and/or lead impedance [BLOCK 418], in this example.

When the signal amplitude is evaluated [BLOCK 410], there may be no intrinsic signal detected. In such case, the lead impedance [BLOCK 418] may be evaluated to determine whether a mechanical problem exists. If the signal amplitude is determined to be stable [BLOCK 412], then no mechanical problem may be detected. If the signal amplitude is determined to be abnormal, then the signal morphology [BLOCK 414] may be evaluated.

If the signal morphology is determined to be stable [BLOCK 416], then no mechanical problem may be detected. If the signal morphology is determined to be abnormal, then the lead impedance [BLOCK 418] may be evaluated. If the lead impedance is determined to be normal (e.g., neither high nor low, within a particular range), a partial or total dislodgement of the lead may be diagnosed [BLOCK 420]. In such case, a notification to the patient and/or the physician may be made [BLOCK 422], for example, indicating that a partial or total dislodgement of the lead may exist.

If the lead impedance is determined to be abnormal (e.g., high or low, outside of the particular range), a mechanical problem with the lead other than a dislodgement of the lead may be diagnosed [BLOCK 424]. In such case, a notification to the patient and/or the physician may be made [BLOCK 426], for example, indicating that a broken conduction wire (high impedance) or an insulation breach (low impedance) may exist in the lead.

It should be understood that other diagnostic algorithms or processes may be performed, for example, based on the monitored parameter that is determined to be abnormal [BLOCK 400]. For example, various processes may be envisioned in view of the matrix 500 illustrated in FIG. 6.

As discussed above, the matrix 500 may be stored in the memory 94 or otherwise accessible to the microcontroller 60 of the device 10. In this example, the first two columns include various changes or conditions that may occur in the operation of the device 10. Thus, the first two columns correspond to monitored parameters (e.g., amplitude, conduction interval and morphology). The third column of the matrix includes corresponding values of the impedance. The combination of one or both conditions in the first two columns and the value of the impedance in the third column correspond to the diagnosis listed in fourth column for the respective row. Thus, the matrix 500 allows the microcontroller 60 to determine a diagnosis from the fourth column based on the existence of the condition(s) in one or both of the first two columns and the value of the impedance in the third column. Depending on the indication for pacing therapy, not all patients may have an intrinsic signal (such as in complete heart block) and the sensing signal may be absent. If, in the baseline testing, there is no morphology template to be used in the algorithm, the algorithm may rely on changes in capture threshold and impedance measurements. Wherever possible, the system may utilize all three measurements to make a diagnosis.

Although the present invention has been described with reference to preferred embodiments, persons skilled in the art will recognize that changes may be made in form and detail without departing from the spirit and scope of the invention.

What is claimed is:

1. A method for diagnosing an implantable cardiac device including a plurality of implanted leads, the method comprising:
    monitoring a plurality of parameters associated with the plurality of implanted leads, the plurality of parameters including a conduction timing interval between leads;
    detecting a change in the conduction timing interval between leads;
    evaluating at least one of the other parameters upon detection of the change; and
    diagnosing a problem with the implantable cardiac device based on the detected change and the evaluation.

2. The method of claim 1, further comprising providing a notification of the problem to an external device.

3. The method of claim 1, wherein the plurality of parameters further includes at least one of a signal amplitude(s), morphology of a signal, capture threshold and impedance.

4. The method of claim 1, wherein diagnosing the problem with the implantable cardiac device comprises identifying dislodgement of one of the implanted leads.

5. The method of claim 4, further comprising providing a notification of the dislodgement to an external device.

6. The method of claim 1, wherein diagnosing the problem with the implantable cardiac device comprises identifying a mechanical problem other than dislodgement of one of the implanted leads.

7. The method of claim 6, wherein the mechanical problem other than dislodgement of one of the implanted leads comprises one of an insulation breach of a lead and a conductor coil fracture of a lead.

8. The method of claim 7, further comprising providing a notification of the insulation breach or the conductor coil fracture to an external device.

9. The method of claim 1, wherein diagnosing the problem with the implantable cardiac device comprises differentiating dislodgement of one of the implanted leads from a different mechanical problem.

10. The method of claim 1, wherein diagnosing the problem with the implantable cardiac device comprises accessing a matrix of parameter changes, parameter evaluation values, and diagnoses associated with combinations of the parameter changes and parameter evaluation values.

11. A system for diagnosing an implantable cardiac device including a plurality of implanted leads, the system comprising:
    an implantable pacing device; and
    a processor configured to:
        monitor a plurality of parameters associated with the plurality of implanted leads, the plurality of parameters including a conduction timing interval between leads;
        detect a change in the conduction timing interval between leads;

evaluating at least one of the other parameters upon detection of the change; and diagnose a problem with the implantable cardiac device based on the detected change and the evaluation.

12. The system of claim 11, further comprising communication circuitry coupled to the processor and configured to provide a notification of the problem to an external device.

13. The system of claim 11, wherein the processor is further configured to monitor and evaluate at least one of a signal amplitude(s), morphology of a signal, capture threshold and impedance.

14. The system of claim 11, wherein the processor is configured to identify dislodgement of one of the implanted leads.

15. The system of claim 14, further comprising communication circuitry coupled to the processor and configured to provide a notification of the dislodgement to an external device.

16. The system of claim 11, wherein the processor is configured to identify a mechanical problem other than dislodgement of one of the implanted leads.

17. The system of claim 16, wherein the processor is configured to identify at least one of an insulation breach of a lead and a conductor coil fracture of a lead.

18. The system of claim 17, further comprising communication circuitry coupled to the processor and configured to provide a notification of the insulation breach and/or the conductor coil fracture to an external device.

19. The system of claim 11, wherein the processor is configured to differentiate dislodgement of one of the implanted leads from a different mechanical problem.

20. The system of claim 11, further comprising a storage element coupled to the processor, the storage element storing a matrix of parameter changes, parameter evaluation values, and diagnoses associated with combinations of the parameter changes and parameter evaluation values, wherein the processor is configured to diagnose the problem with the implantable cardiac device by accessing the matrix.

* * * * *